United States Patent
Okano et al.

(10) Patent No.: US 10,041,040 B2
(45) Date of Patent: Aug. 7, 2018

(54) CULTURE METHOD OF EMBRYOID BODIES AND/OR NEURAL STEM CELLS DERIVED FROM HUMAN DIFFERENTIATED CELL-DERIVED PLURIPOTENT STEM CELLS

(75) Inventors: Hideyuki Okano, Tokyo (JP); Yohei Okada, Tokyo (JP); Masaya Nakamura, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 13/147,558

(22) PCT Filed: Feb. 3, 2010

(86) PCT No.: PCT/JP2010/000640
§ 371 (c)(1),
(2), (4) Date: Sep. 29, 2011

(87) PCT Pub. No.: WO2010/090007
PCT Pub. Date: Aug. 12, 2010

(65) Prior Publication Data
US 2012/0009157 A1 Jan. 12, 2012

Related U.S. Application Data

(60) Provisional application No. 61/206,711, filed on Feb. 3, 2009.

(51) Int. Cl.
*C12N 5/00* (2006.01)
*C12N 5/079* (2010.01)
*A61K 35/12* (2015.01)

(52) U.S. Cl.
CPC ............ *C12N 5/0618* (2013.01); *A61K 35/12* (2013.01); *C12N 2501/115* (2013.01); *C12N 2501/235* (2013.01); *C12N 2506/45* (2013.01)

(58) Field of Classification Search
None
See application file for complete search history.

(56) References Cited

U.S. PATENT DOCUMENTS

| 5,968,829 A | 10/1999 | Carpenter |
| 6,103,530 A | 8/2000 | Carpenter |
| 2002/0164791 A1 | 11/2002 | Van Der Kooy et al. |
| 2003/0036195 A1 | 2/2003 | Studer et al. |
| 2007/0054398 A1 | 3/2007 | Endo et al. |
| 2009/0068742 A1 | 3/2009 | Yamanaka |

FOREIGN PATENT DOCUMENTS

| JP | 2002/518990 | 7/2002 |
| JP | 2003/189847 | 7/2003 |
| JP | 2006/55069 | 3/2006 |
| WO | WO 02/26941 A2 | 4/2002 |
| WO | WO 2004/074465 A1 | 9/2004 |
| WO | WO-2005/089420 A2 | 9/2005 |
| WO | WO-2007069666 A1 | 6/2007 |

OTHER PUBLICATIONS

Baharvand et al., Differentiation, 72:224-229, 2004.*
Hitoshi S, Symposium 4-2: New Strategy for Nerve Regeneration, Clinical Neurology, 43, pp. 827-829, May 16, 2003 (English translation).*
Lake et al., Journal of Cell Science, 113:555-566, Jan. 19, 2000.*
Shimazaki et al., J Neuroscience, 21(19):7642-7653 Oct. 2001.*
Wright et al., J Neurochemistry, 86:179-195, 2003.*
Galli et al., Developmental Neuroscience; 22(1-2): 86-95, Jan./Feb. 2000.*
Ramirez et al. Stem Cells, 29:1469-1474. (Year: 2011).*
He et al., "Effect of Leukemia Inhibitory Factor on Embryonic Stem Cell Differentiation: Implications for Supporting Neuronal Differentiation," *Acta Pharmacologica Sinica* 27(1) 80-90 (2006).
Muira et al., "Variation in the Safety of Induced Pluripotent Stem Cell Lines," *Nat. Biotechnol.* 27(8): 743-745 (2009).
Nakagawa et al., "Generation of Induced Pluripotent Stem Cells Without Myc from Mouse and Human Fibroblasts," *Nat. Biotechnol.* 26(1): 101-106 (2008).
Okada et al., "Spatiotemporal Recapitulation of Central Nervous System Development by Murine Embryonic Stem Cell-Derived Neural Stem/Progenitor Cells," *Stem Cells* 26(12): 3086-3098 (2008).
Okano et al., "Regeneration Using Embryonic Stem Cells and Neural Stem Cells," *Research on Diagnosis and Therapy of Amyotrophic Lateral Sclerosis* pp. 17-20 (2008). (In Japanese).
Okano et al., "Strategies Toward CNS-Regeneration Using Induced Pluripotent Stem Cells," *Genome Inform.* 23(1): 217-220 (2009).
International Preliminary Report on Patentability for International Patent Application No. PCT/JP2010/000640, dated Jun. 16, 2011 (date of completion of report) and Jun. 28, 2011 (date of mailing of report).
International Search Report for International Patent Application No. PCT/JP2010/000640, dated Apr. 19, 2010 (date of completion of search) and Apr. 27, 2010 (date of mailing of report).
Aoi et al., "Generation of pluripotent stem cells from adult mouse liver and stomach cells," *Science* 321: 699-702 (2008).

(Continued)

*Primary Examiner* — Kimberly Ballard
*Assistant Examiner* — Stacey N MacFarlane
(74) *Attorney, Agent, or Firm* — Clark & Elbing LLP

(57) ABSTRACT

A method for differentiating a human differentiated cell-derived pluripotent stem cell into a neural stem cell is provided, which includes the steps of: making an embryoid body from the human differentiated cell-derived pluripotent stem cell; and culturing the embryoid body in a medium containing LIF to differentiate into a neural stem cell, so that, when the neural stem cell is allowed to differentiate in vitro after multiple subculturing of the neural stem cell, it differentiate mainly into neurons but substantially not into glial cells.

8 Claims, 6 Drawing Sheets

(56) References Cited

OTHER PUBLICATIONS

Basso et al., "A sensitive and reliable locomotor rating scale for open field testing in rats," *Journal of Neurotrauma* 12: 1-21 (1995).
Blelloch et al., "Generation of induced pluripotent stem cells in the absence of drug selection," *Cell Stem Cell* 1: 245-247 (2007).
Meissner et al., "Direct reprogramming of genetically unmodified fibroblasts into pluripotent stem cells," *Nature Biotechnology* 25: 1177-1181 (2007).
Naka et al., "Requirement for COUP-TFI and II in the temporal specification of neural stem cells in CNS development," *Nature Neuroscience* 11: 1014-1023 (2008).
Okada et al., "Spatiotemporal recapitulation of central nervous system development by murine embryonic stem cell-derived neural stem/progenitor cells," *Stem Cells* 26: 3086-3098 (2008).
English Translation of Okano et al., "Regeneration Using Embryonic Stem Cells and Neural Stem Cells," *Research on Diagnosis and Therapy of Amyotrophic Lateral Sclerosis* pp. 17-20 (2008).
Okita et al., "Generation of germline-competent induced pluripotent stem cells," *Nature* 448: 313-317 (2007).
Suemori et al., "Efficient establishment of human embryonic stem cell lines and long-term maintenance with stable karyotype by enzymatic bulk passage," *Biochemical and Biophysical Research Communications* 345: 926-932 (2006).
Takahashi et al., "Induction of pluripotent stem cells from mouse embryonic and adult fibroblast cultures by defined factors," *Cell* 126: 663-676 (2006).
Takahashi et al., "Induction of pluripotent stem cells from adult human fibroblasts by defined factors," *Cell* 131: 861-872 (2007).
Temple, "The development of neural stem cells," *Insight Review Articles* 414: 112-117 (2001).
Wernig et al., "c-Myc Is dispensable for direct reprogramming of mouse fibroblasts," *Cell Stem Cell* 2: 10-12 (2008).
Yu et al., "Induced pluripotent stem cell lines derived from human somatic cells," *Science* 318: 1917-1920 (2007).
"Abstracts of the 31st Annual Meeting of the Japan Neuroscience Society, Jul. 9-11, 2008," Neurosci Res. 61S:S1-S281(2008).
Bauer, "Cytokine control of adult neural stem cells," Ann N Y Acad Sci. 1153:48-56 (2009).
Chamberlain et al., "Induced pluripotent stem (iPS) cells as in vitro models of human neurogenetic disorders," Neurogenetics. 9:227-235 (2008).
Lowry et al., "Generation of human induced pluripotent stem cells from dermal fibroblasts," Proc Natl Acad Sci U S A. 105(8):2883-2888 (2008).
Maherali et al., "Directly reprogrammed fibroblasts show global epigenetic remodeling and widespread tissue contribution," Cell Stem Cell. 1:55-70 (2007).

Osahiko et al., "Therapeutic effect of pre-evaluated 'safe' iPS derived neurospheres for spinal cord injury: Paper #48," <http://journals.lww.com/spinejournalabstracts/Citation/2009/10001/Therapeutic_Effect_of_Pre_Evaluated_Safe_iPS>, Dec. 5, 2009 (3 pages).
Park et al., "Reprogramming of human somatic cells to pluripotency with defined factors," Nature. 451:141-147 (2008).
Pitman et al., "LIF receptor signaling modulates neural stem cell renewal," Mol Cell Neurosci. 27:255-266 (2004).
Shimazaki et al., "The ciliary neurotrophic factor/leukemia inhibitory factor/gp130 receptor complex operates in the maintenance of mammalian forebrain neural stem cells," J Neurosci. 21(19):7642-7653 (2001).
Wernig et al., "Neurons derived from reprogrammed fibroblasts functionally integrate into the fetal brain and improve symptoms of rats with Parkinson's disease," Proc Natl Acad Sci U S A. 150(15):5856-5861 (2008).
Wright et al., "Gene expression in human neural stem cells: effects of leukemia inhibitory factor," J Neurochem. 86:179-195 (2003).
Okada et al., "Spatiotemporal recapitulation of central nervous system development by murine embryonic stem cell-derived neural stem/progenitor cells," Stem Cells. 26:3086-98 (2008) (Supplemental Materials and Methods, 22 pages).
Hitoshi et al., "Primitive neural stem cells from the mammalian epiblast differentiate to definitive neural stem cells under the control of Notch signaling," Genes Dev. 18(15):1806-11 (2004).
Carpenter et al., "In vitro expansion of a multipotent population of human neural progenitor cells," Experimental Neurology 158:265-278 (1999).
Okano, "Neurologic regenerative medicine using embryonic stem cells and neural stem cells," Health and Labour Sciences Research Grants (Research on rare and intractable diseases) Research group for methods of diagnostic imaging and treatment for amyotrophic lateral sclerosis, H17-19 General Research Report, pp. 17-20 (2008).
"Neural Stem Cell," The Dictionary of Molecular and Cellular Biology (Second Edition), Tokyo Kagaku Dojin Co. Ltd., pp. 462-463, published Oct. 10, 2008 (1 page).
Huang, "Relationship between embryoid body formation and hematopoietic differentiation of mouse embryonic stem cells," International Journal of Blood Transfusion and Hematology 31(4):364-368 (2008) (14 pages).
Huang et al., "Effects of embryoid bodies in different stages on embryonic stem cells in hematopoietic differentiation," International Journal of Blood Transfusion and Hematology 31(3):212-218 (2008) (13 pages).
Qin et al., "Developmental characteristics and gene expression patterns of mouse embryonic stem cells-derived embryoid bodies in vitro," Acta anatomica sinica 39(4):547-551 (2008) (13 pages).

* cited by examiner

[Fig. 1A]
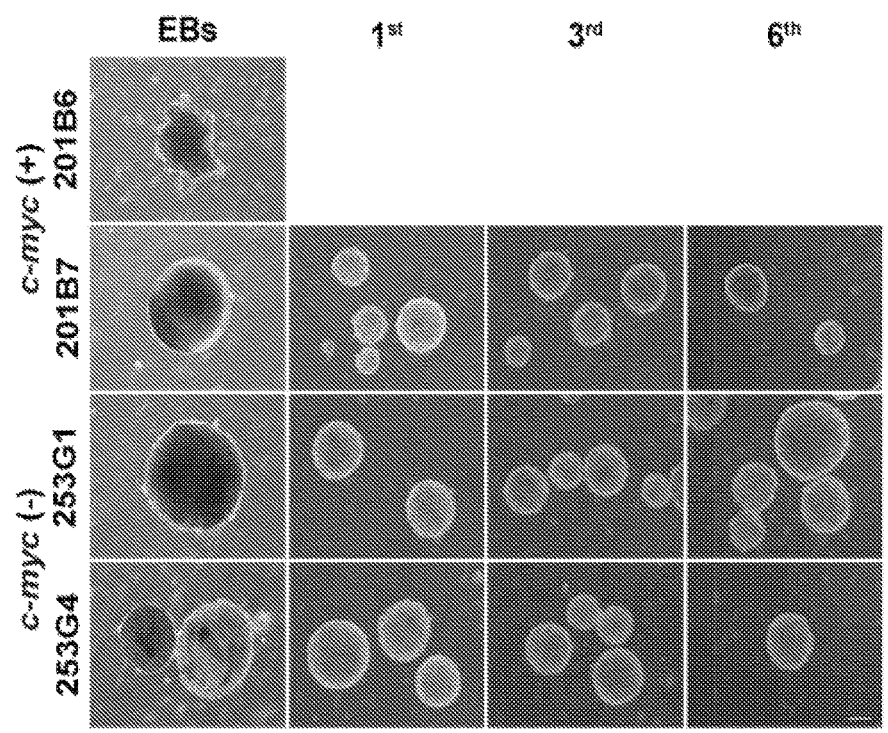

[Fig. 1B]
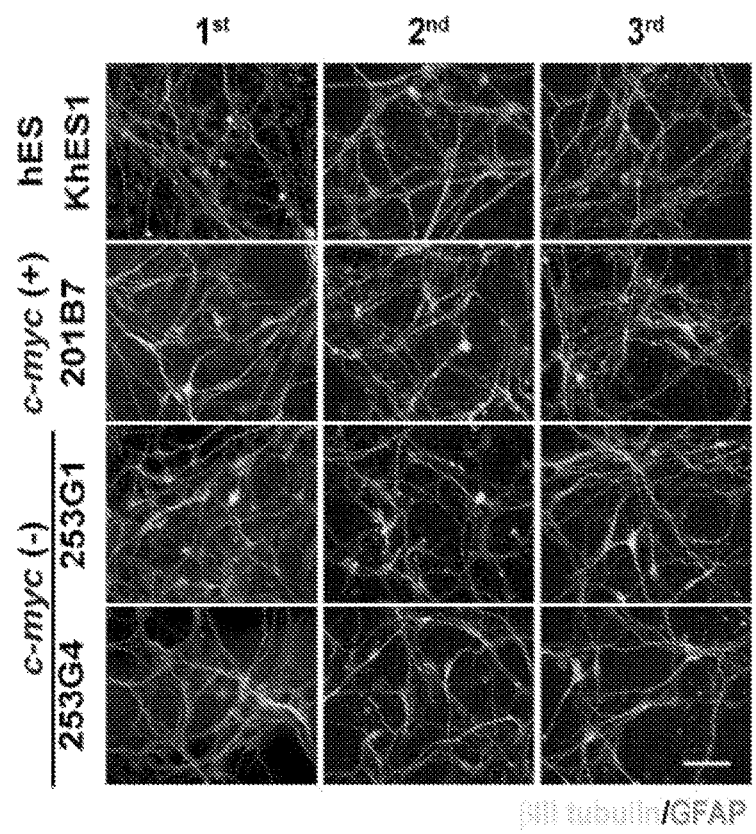

[Fig. 2]
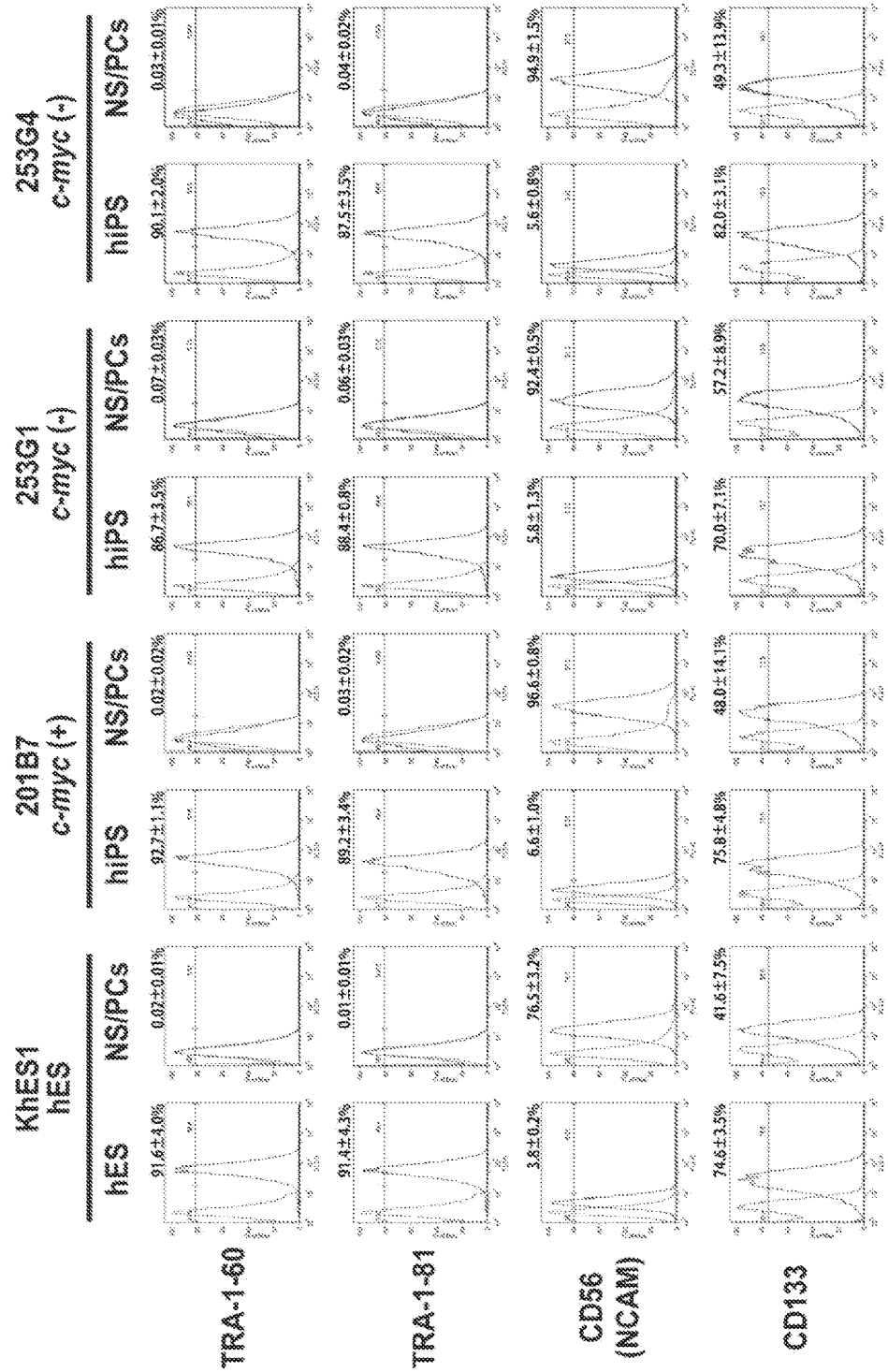

[Fig. 3]
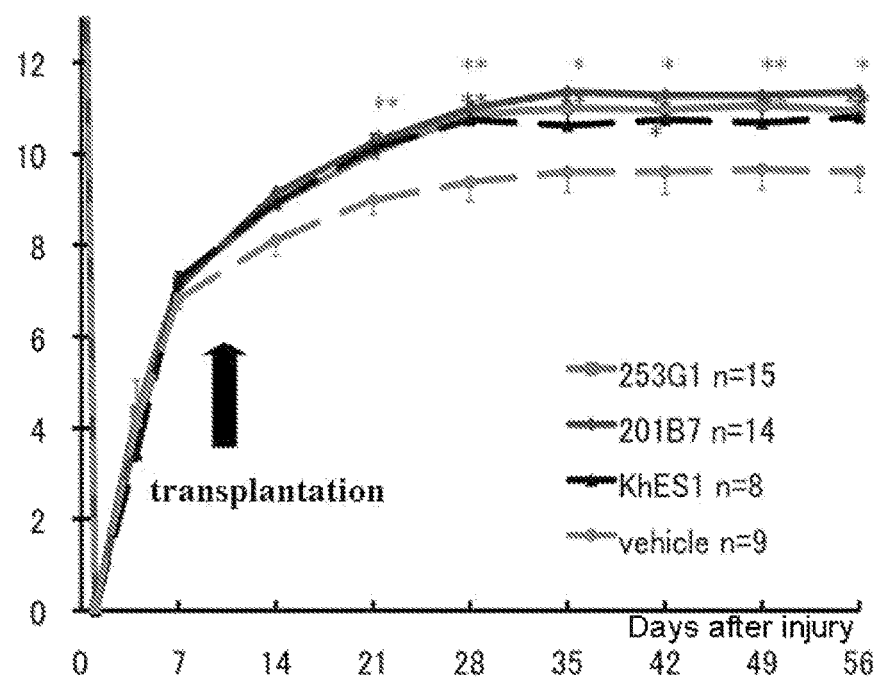

[Fig. 4]
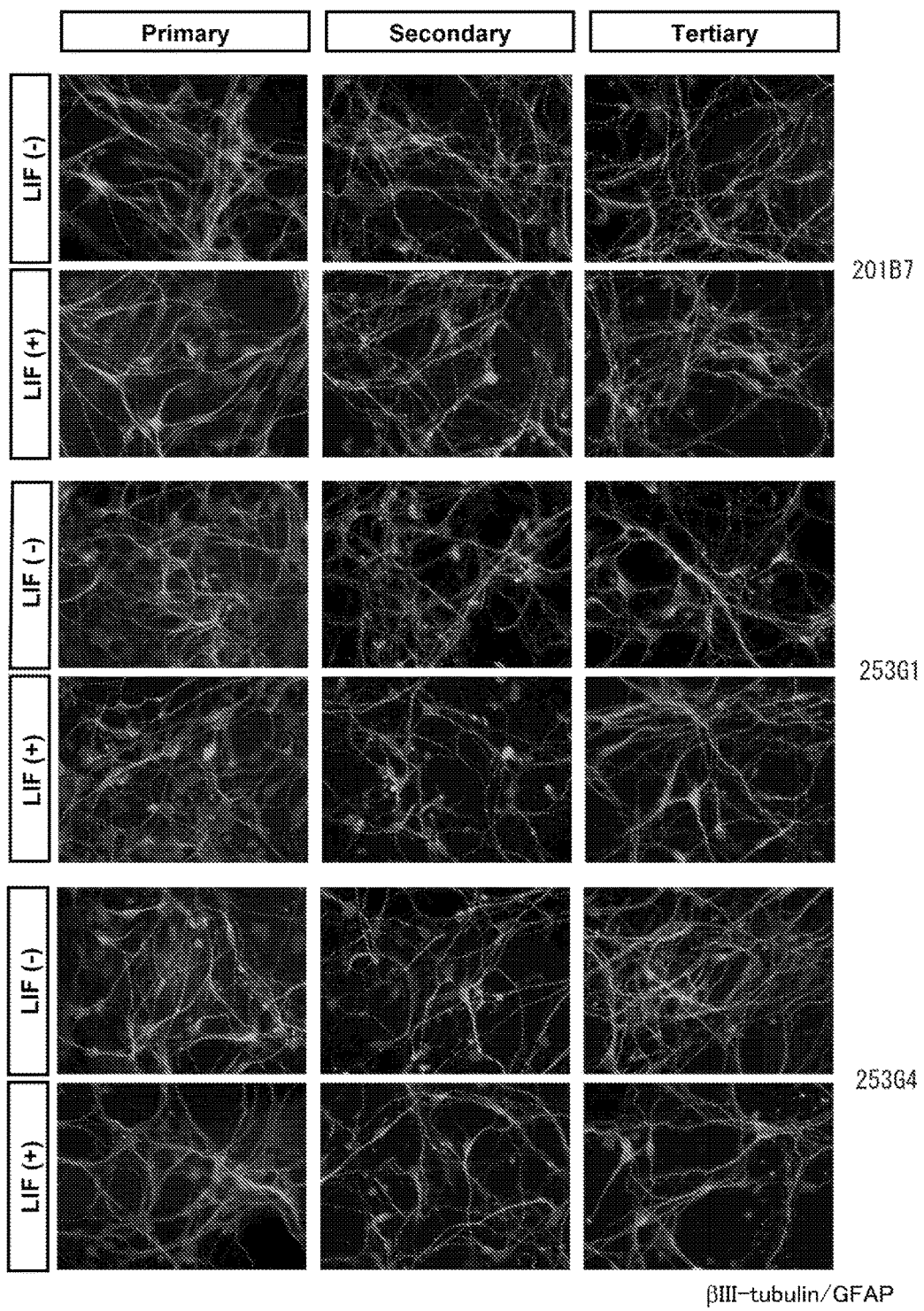

[Fig. 5]
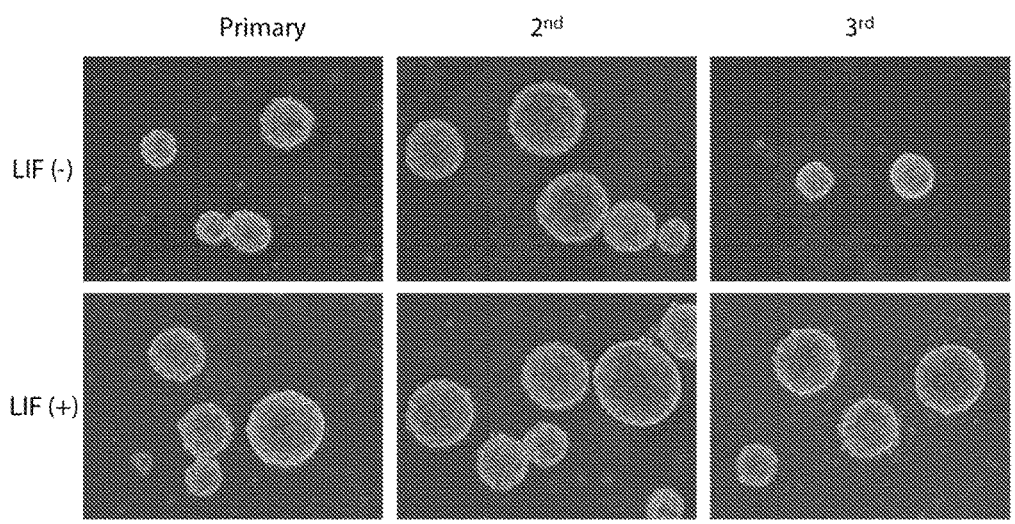
[Fig. 6]
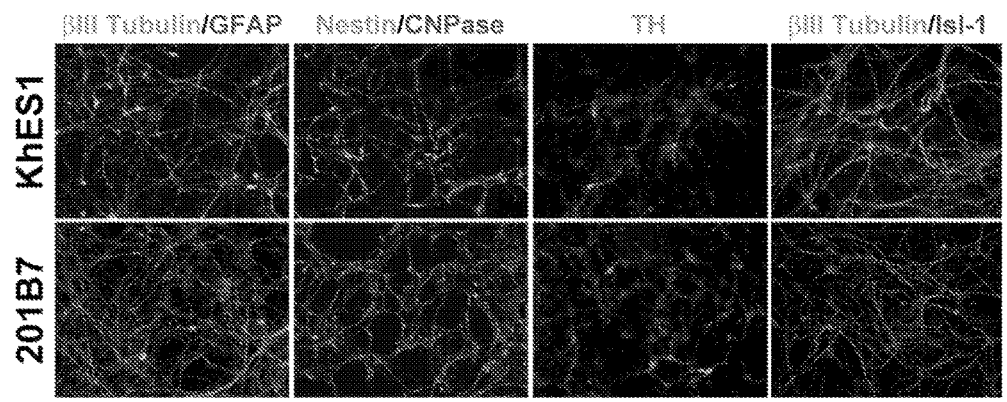

ical Problems

CULTURE METHOD OF EMBRYOID BODIES AND/OR NEURAL STEM CELLS DERIVED FROM HUMAN DIFFERENTIATED CELL-DERIVED PLURIPOTENT STEM CELLS

CROSS-REFERENCE TO RELATED APPLICATIONS

This application is a U.S. National Stage of International Patent Application No. PCT/JP2010/000640, filed Feb. 3, 2010, which claims the benefit of U.S. Provisional Application No. 61/206,711, filed on Feb. 3, 2009.

TECHNICAL FIELD

The present invention relates to culture method of embryoid bodies and/or neural stem cells derived from human differentiated cell-derived pluripotent stem cells.

BACKGROUND ART

In recent years, it has become possible to obtain cells having pluripotency similar to embryonic stem cells (hereafter referred to as ES cells) by selecting cells expressing Fbxo15 gene from somatic cells such as fibroblasts in which Oct3/4 gene, Sox2 gene, Klf4 gene, and c-myc gene have been introduced and expressed (International Patent Application Publication No. WO2007/069666; Takahashi K, and Yamanaka S. (2006) Cell 126:663-676). It is considered that if pluripotent stem cells derived from somatic cells thus obtained are used in regenerative medicine, the cells of a patient can become transplanted to the patient himself so that rejection problems would be smaller than when ES cells are used.

While somatic cell-derived pluripotent stem cells (hereafter referred to as induced pluripotent stem cells, or iPS cells) established by using Fbxo15 gene as a marker were closely similar to embryonic stem cells in terms of cell morphology, proliferation ability, differentiation ability etc., they were different from ES cells in some characteristics such as gene expression and DNA methylation patterns. Then, the cells were selected by using the expression of the Nanog gene as a marker, and iPS cells having pluripotency more similar to ES cells were established (Okita K, Ichisaka T, and Yamanaka S. (2007) Nature 448:313-317).

Later, iPS cells were isolated using changes in cell morphology as a marker, instead of the expression of Fbxo15 gene or Nanog gene (Meissner A, Wernig M, and Jaenisch R. (2007). Nat Biotechnol 25:1177-1181). iPS cells were also established by using N-myc instead of c-myc (Blelloch R, Venere M, Yen J, Ramalho-Santos M. (2007) Cell Stem Cell 1:245-247). Further, in mice as well as in humans, iPS cells were established by introducing the three genes of Oct3/4, Sox2 and Klf4, without using c-myc gene (Nakagawa M, Koyanagi M, Tanabe K, Takahashi K, Ichisaka T, Aoi T, Okita K, Mochiduki Y, Takizawa N, and Yamanaka S. (2008). Nat Biotechnol 26:101-106; Wernig M, Meissner A, Cassady J P, and Jaenisch R. (2008) Cell Stem Cell 2:10-12). In addition, iPS cells were established from hepatocytes and gastric epithelial cells, besides fibroblasts (Aoi T, Nakagawa M, Ichisaka T, Okita K, Takahashi K, Chiba T, and Yamanaka S. (2008) Science (Feb. 14, 2008) (published online).).

Meanwhile, there has also been a growing body of studies using human cells. Human iPS cells were established by introducing into fibroblasts four genes of Oct3/4, Sox2, Nanog, and lin28 (Yu J, Vodyanik M A, Smuga-Otto K, Antosiewicz-Bourget J, Frane J L, Tian S, Nie J, Jonsdottir G A, Ruotti V, Stewart R, Slukvin I I, and Thomson J A. (2007) Science 318:1917-1920) the same combination of genes (i.e. Oct3/4 gene, Sox2 gene, Klf4 gene, and c-myc gene) as used for establishment of mouse iPS cells (Takahashi K, Tanabe K, Ohnuki M, Narita M, Ichisaka T, Tomoda K, and Yamanaka S. (2007) Cell 131:861-872).

Since iPS cells can be produced using cells derived from a patient to be treated, artificial organs and the like which are escaped from rejection are expected to be produced by using iPS cells in the field of regenerative medicine.

SUMMARY OF INVENTION

Technical Problems

The object of the present invention is to develop culture conditions of embryoid bodies and/or neural stem cells derived from iPS cells, which are appropriate for neuronal differentiation of the neural stem cells.

Solution to Problem

In one embodiment of the present invention, an agent for culture of an embryoid body derived from a human differentiated cell-derived pluripotent stem cell and/or a neural stem cell derived from the embryoid body contains LIF.

In another embodiment of the present invention, a method for differentiating an embryoid body derived from a human differentiated cell-derived pluripotent stem cell into a neural stem cell includes the step of culturing the embryoid body in a medium containing LIF to differentiate into a neural stem cell. This method may further include the step of subculturing the neural stem cell in a medium containing LIF.

In another embodiment of the present invention, a method for culturing a neural stem cell derived from a human differentiated cell-derived pluripotent stem cell includes the step of culturing the neural stem cell in a medium containing LIF.

In another embodiment of the present invention, a method of preparing a medicine for treating nerve injury, the medicine comprising a neural stem cell derived from a human differentiated cell-derived pluripotent stem cell, includes the steps of: culturing an embryoid body derived from the human differentiated cell-derived pluripotent stem cell in a medium containing LIF to differentiate into a neural stem cell; and preparing the medicine using the neural stem cell. This method may further include the step of subculturing the neural stem cell in a medium containing LIF.

In another embodiment of the present invention, a method of preparing a medicine for treating nerve injury, the medicine containing a neural stem cell derived from a human differentiated cell-derived pluripotent stem cell includes the steps of: culturing a neural stem cell derived from a human differentiated cell-derived pluripotent stem cell in a medium containing LIF; and preparing the medicine using the neural stem cell.

In any of the above embodiments, the LIF concentration is preferably from 10 to 100 ng/ml.

BRIEF DESCRIPTION OF DRAWINGS

FIG. 1A shows the micrographs indicating the morphologies of the neurospheres derived from human iPS cells in one example of the present invention.

FIG. 1B shows the micrographs indicating the differentiation abilities of the neurospheres derived from human iPS cells in one example of the present invention.

FIG. 2 shows the results of FACS analyses to examine the presence of undifferentiated cells in the neurospheres derived from human iPS cells in one example of the present invention. Red lines indicate the negative controls.

FIG. 3 shows a graph indicating the results of motor function analyses evaluated by the BBB scores of the transplanted mice.

FIG. 4 shows the micrographs indicating the differentiation abilities of the primary, secondary and tertiary neurospheres derived from human iPS cells, which have been cultured with or without LIF, in one example of the present invention.

FIG. 5 shows the micrographs indicating the morphologies of the primary, secondary and tertiary neurospheres derived from human iPS cells, which have been cultured with or without LIF, in one example of the present invention.

FIG. 6 shows the micrographs indicating the subtypes of the neurons differentiated from tertiary neurospheres derived from human iPS 201B7 cells, which have been cultured with LIF, in one example of the present invention.

DESCRIPTION OF EMBODIMENTS

==Human Differentiated Cell-Derived Pluripotent Stem Cells==

A human differentiated cell-derived pluripotent stem cell refers to a human cell having pluripotency and self-reproducing ability, which is artificially induced by reprogramming a differentiated cell other than germline cells such as egg cells, sperm cells and their precursor cells such as oogonia and spermatogonia or undifferentiated cells derived from embryos at early stages of development such as embryonic stem cells. The differentiated cell may be derived from an embryo, a fetus, or an adult. The characteristics of the differentiated cell is not particularly limited as long as the cell has at least partly lost intrinsic totipotency that a fertilized egg or an ES cell has. Examples of such a differentiated cell include fibroblasts, epithelial cells, hepatocytes, etc.

The method for reprogramming the differentiated cell is not particularly limited, but it is preferred that introduction of nuclear reprogramming factors into the cell induces the reprogramming so that it possesses pluripotency and self-reproduction ability. For example, the reprogramming method as described in Takahashi et al. (NPL 8) can be used for the reprogramming. This publication is incorporated herein by reference.

The nuclear reprogramming factor is not particularly limited, but preferred is a combination of products of the genes selected from each one member of the Oct gene family, Klf gene family, and Sox gene family. In terms of efficiency of establishment of iPS cells, more preferred is a combination further containing a gene product of one member of the myc gene family. The genes belonging to the Oct gene family include Oct3/4, Oct1A, Oct6, etc.; the genes belonging to the Klf gene family include Klf1, Klf2, Klf4, Klf5, etc.; the genes belonging to the Sox gene family include Sox1, Sox2, Sox3, Sox7, Sox15, Sox17, Sox18, etc.; and the genes belonging to the myc gene family include c-myc, N-myc, L-myc, etc. In some cases, gene products of the myc gene family may be substituted with a cytokine such as SCF, bFGF, or a chemical compound such as azacitidine and sodium valproate (VPA).

Examples of the nuclear reprogramming factors other than the above-described combination include a combination containing Nanog gene and lin-28 gene in addition to a gene from the Oct gene family and a gene from the Sox gene family. It should be noted that when introducing such factors into the cells, another type of gene product may be introduced in addition to the genes in the above-described combinations. Examples of such type of gene products include an immortalization-inducing factor such as TERT.

Since all of the above-mentioned genes are highly conserved among the vertebrates, a gene referred herein includes its homologues and orthologues unless the name of a particular animal is indicated. Moreover, mutated genes including polymorphic genes are also encompassed as long as they have a function comparable to that of the wild-type gene product.

==The Method for Preparing Human Differentiated Cell-Derived Pluripotent Stem Cells==

To prepare a human differentiated cell-derived pluripotent cell by using nuclear reprogramming factors, in the case the nuclear reprogramming factor is a protein functioning in a cell, a gene encoding the protein is preferably incorporated into an expression vector, which is introduced into a target differentiated cell such as a somatic cell, so that the protein is intracellularly expressed (the gene transfer method). The expression vector to be used is not particularly limited, but preferred is a viral vector, particularly preferred is a retroviral vector or a lentiviral vector, and most preferred is a Sendai virus vector. The nuclear reprogramming factor may be introduced into cells by binding a peptide called Protein Transduction Domain (PTD) to the protein, which is added to a culture medium (the protein transduction method). In the case the protein is secreted extracellularly, the factor may be added to the culture medium of the differentiated cell during the preparation of the differentiated cell-derived pluripotent stem cell. If the factor is expressed in the differentiated cell to be reprogrammed, it does not need to be introduced from outside. Also, if a chemical compound capable of substituting for the function of a particular nuclear reprogramming factor is present, it may be used in place of the nuclear reprogramming factor. The chemical compound includes Tranylcypromine, CHIR99021, SB431542, PD0325901, thiazovivin but is not limited thereto.

Then, in the differentiated cell into which nuclear reprogramming factors have been introduced, a colony of cells maintaining their undifferentiated state, or a colony of cells expressing an undifferentiation marker gene such as Fbxo15 gene or Nanog gene may be selected and isolated while the cells are kept alive. Alternatively, the differentiated cell may have been co-transfected with a retroviral vector to express GFP (green fluorescent protein) or dsRed (red fluorescent protein) as a marker and then a colony of cells in which the expression of the marker is silenced may be selected.

By using any of the abovementioned markers, the cells being reprogrammed and maintaining undifferentiated state can be selected and isolated from the human differentiated cell into which the nuclear reprogramming factors have been introduced, and the established cell population may be used as the human differentiated cell-derived pluripotent cell.

==The Medicine for Treating Nerve Injury==

The differentiated cell-derived pluripotent cell can be used to make a medicine for treating nerve injury. The method for making an agent of the medicine for treating nerve injury may be based on a method that has been developed to use embryonic stem cells as an agent for treating nerve injury, as described in Okada et al. (Okada Y, Matsumoto A, Shimazaki T, Enoki R, Koizumi A, Ishii S, Itoyama Y, Sobue G, Okano H. (2008) Stem Cells. vol. 26, pp. 3086-98), which is incorporated herein by reference.

The agent for treating nerve injury may contain another component such as a buffer solution containing salt and/or antibiotics, in addition to the human differentiated cell-derived pluripotent cell. The nervous tissue as a target of the treatment is not particularly limited, being either the central nervous system such as the brain or the spinal cord or the peripheral nervous system. Further, the disease to be treated is not limited to any specific symptom but includes a traumatic disease such as a spinal cord injury; a neurodegenerative disease such as amyotrophic lateralsclerosis, Alzheimer's disease, Parkinson's disease, progressive supranuclear palsy, Huntington disease, multiple system atrophy, and spino-cerebellar degeneration; necrosis of nerve cells resulting from cerebral infarction, intracerebral hemorrhage, etc.), and not limited to any specific cause but includes the primary cause being associated with injury, cerebral infarction, etc., and the secondary cause being associated with infection, tumor, etc., as long as it is a disease or a pathological condition in which nerve cells are damaged.

The human differentiated cell-derived pluripotent cell may be administered to a human as it is, but to enhance its ability to differentiate into neural cells, an embryoid body (EB) may be formed and then administered. The EB preferably contains neural stem cells. It is more preferred that the neural stem cells in the EB are amplified in a culture condition for growing the neural stem cells prior to the administration.

The medium for the culture in which the EB is formed from the human differentiated cell-derived pluripotent cell is not limited but may be a DMEM/F12 medium containing KSR (Knockout Serum Replacement), NEAA (non-essential amino acid), and 2-ME (2-mercaptoethanol). The concentrations of KSR, NEAA and 2-ME are not limited but are preferentially 5% or less, 0.1 mM and 0.1 mM, respectively. The formed EB may be cultured in a differentiation medium such as a serum-free medium supplemented with FGF-2 (10 to 100 ng/ml) to differentiate into neural stem cells in the form of neurospheres. The culture medium of the neurosphere is not limited but the same serum-free medium supplemented with FGF-2 (10 to 100 ng/ml) can be used to culture the neurospheres. The primary neurospheres containing the primary neural stem cell can be subcultured by dispersing and replating them onto a culture dish so that they proliferate to form secondary neurospheres containing the secondary neural stem cell; and this subculture process can be repeated to make higher-order neurospheres containing higher-order neural stem cells. The neural stem cells are thus formed can be administered to a human, preferably after dispersion of the neurospheres. The neural stem cells to be administered may or may not possess an ability to differentiate into glial cells in vitro. LIF can be added to the medium for either or both of the EB and the neural stem cell and its appropriate concentration can be determined by the artisan but 1 ng/ml or more is preferred, 5 ng/ml or more is more preferred and 10 ng/ml or more is most preferred; 1000 ng/ml or less is preferred, 500 ng/ml or less is more preferred and 100 ng/ml or more is most preferred; and 1-1000 ng/ml is preferred, 5-500 ng/ml is more preferred and 10-100 ng/ml is most preferred.

When the EB or the neural stem cells is cultured in the medium without LIF, the neural stem cell has obtained a differentiation potential into neuronal cells and glial cells. However, when the EB and the neural stem cells are cultured in the medium with LIF, the neural stem cells have a differentiation potential mainly into neuronal cells but substantially not into glial cells. In the culture condition with LIF, even after subculturing the neural stem cell many times, the neural stem cells still keep the differentiation potential that they can differentiate mainly into neuronal cells but substantially not into glial cells in vitro. It is known that the neural stem cells experience the expansion phase, the neurogenic phase and the gliogenic phase in this order during their development in the CNS (Temple, S., Nature vol. 414. p. 112-117, 2001). Therefore, the neural stem cells can maintain their differentiation potential of their young stages in vitro by being cultured under the existence of LIF. In addition, the neuronal cells derived from the neural stem cells thus obtained contain early-born neurons such as TH-positive or Is1-positive neurons, which are not generally contained in those derived from the neural stem cells cultured without LIF or those obtained from fetus after the mid-gestation (Nature neurosci. vol. 11, p. 1014-1023, 2008). This is consistent with the fact that they can keep their potential of their young stage under the existence of LIF. Furthermore, the neural stem cells cultured with LIF form bigger neurospheres in average than those cultured without LIF, probably because the former grows better than the latter.

The method for in vitro differentiation of the neural stem cells is not particularly limited, and the neurospheres may be cultured in any known differentiation-inducing medium, whose preferred example is a DMEM:F-12 medium supplemented with glucose, glutamine, insulin, transferrin, progesterone, putrescine and selenium chloride (i.e. the medium for proliferating neural stem cells without FGF and heparin). Sonic hedgehog protein may be either present or absent therein. The cells are preferably incubated under the conditions of 5% $CO_2$ at 35 to 40° C. for 5 to 7 days.

The differentiated cell-derived pluripotent cell, the EB cell or the neural stem cell may be administered either directly or indirectly. For a direct administration, cells may be transplanted to the site of nerve injury, for example. For an indirect administration, cells may be injected intravenously or intraspinally and delivered to the affected site through the circulation of blood or cerebrospinal fluid.

EXAMPLES

==Cells==

In this example, the differentiated cell-derived pluripotent cells were either the cells (253G4, 253G1) obtained by introducing the combination of Oct3/4, Sox2 and Klf4 as nuclear reprogramming factors to human embryonic fibroblasts, or the cells (201B7, 201B6) obtained by introducing the combination of Oct3/4, Sox2, c-Myc and Klf4 as nuclear reprogramming factors to human embryonic fibroblasts (Yu J et al. (2007). Science 318:1917-1920; Nakagawa M et al., (2008). Nat Biotechnol vol. 26, p. 101-106.), all of which were provided by Kyoto University. As for the control, human ES cells (KhES1) (Suemori H et al., (2006), Biochem. and Biophys. Res. Commun. vol. 345, p. 926-932.) were used.

<Experiment 1> Production of Neural Stem Cells

To enhance the ability of these cells to differentiate into neural cells, embryoid bodies (EBs) were made by culturing the differentiated cell-derived pluripotent cells in suspension with an embryoid-culturing medium supplemented with 5% KSR in a bacterial-culture dish for 30 days. Then, the EBs formed were dispersed and cultured in a serum-free medium supplemented with FGF-2 (20 ng/ml) and LIF (10 ng/ml). In 12 days, the cells derived from the EBs formed neurospheres, which are called as primary neurospheres or iPS-PNSs. It was possible to dissociate these iPS-PNSs and make the neurospheres again under the same conditions repeatedly. In this specification, the neurospheres subcultured at least one time are collectively called as higher-order neurospheres; specifically, the neurosphere subcultured (N−1) times is called as N-th neurosphere.

As shown in FIG. 1A indicating the morphological images of the neurospheres observed under an optical microscope, the neurospheres were formed as the primary neurospheres, the tertiary neurospheres after being subcultured twice, and the 6th neurospheres after being subcultured five times.

The primary to tertiary neurospheres thus obtained were dispersed by treatment with TrypLE Select (or a trypsin solution) and pipetting, seeded in culture dishes double-coated with Poly-L-ornitin and fibronectin and filled with the differentiation-inducing medium, and allowed to differentiate by culturing for 7 to 12 days. As for the differentiation-inducing medium, DMEM:F-12 medium supplemented with glucose, glutamine, insulin, transferrin, progesterone, putrescine and selenium chloride to which B27 supplement was added at 2% (i.e. the medium for proliferating neural stem cells without FGF and heparin) was used, and the cells were incubated under the condition of 5% $CO_2$ at 35 to 40° C. for 10 days. Specimens were then immunostained with an antibody against beta III-tubulin (mouse IgG, SIGMA T8660, 1000-fold dilution), a marker for neurons (indicated by green fluorescence), and an antibody against GFAP (rabbit IgG, DAKO ZO334, 4000-fold dilution), a marker for astrocytes (indicated by red fluorescence), and the cellular morphologies and staining were observed under a fluorescent microscope. Hoechst 33258 was used to counterstain cell nuclei (indicated by blue fluorescence).

As shown in FIG. 1B, from the primary to tertiary neurospheres, substantially only neurons differentiated, and glia did not. Such characteristics of human iPS cells are significantly different from those of mouse iPS cells. In the case of mouse cells, when the primary neurospheres are cultured under the same differentiating conditions, only neurons are differentiated like human cells. However, when the higher-order neurospheres from a mouse which had been subcultured at least once are set under the same differentiating conditions, not only neurons but also glial cells are differentiated.

<Experiment 2> Presence of Undifferentiated Cells in Neurospheres

It is shown below that no undifferentiated cell was found in the tertiary neurospheres (hereafter called as iPS-TNS) which are derived from human iPS cells.

The tertiary neurospheres were dispersed by treatment with TrypLE Select (or a trypsin solution) and pipetting, and antibodies against cell surface antigens (TRA-1-60, TRA-1-81, CD56 or CD133) expressed in undifferentiated cells were applied for FACS analysis. The antibodies TRA-1-60-PE, TRA-1-81-PE and CD56-Alexa488 purchased from BD Inc. were used at 5 ul for $1 \times 10^6$ cells in 50 ul, and the antibody CD133-APC purchased from Milteny Biotech inc. was used at 2 ul for $1 \times 10^6$ cells in 50 ul. In a result as shown in FIG. 2, neither of expressions of TRA-1-60 and TRA-1-81 was observed in the tertiary neurospheres derived from the human iPS cells like the human ES cells. Furthermore, almost all cells expressed CD56, a marker for the neural stem cells.

As described so far, the higher-order neurospheres prepared from human iPS cells have no undifferentiated cells at al, or only in quite small number even if a contamination exists, and therefore are useful for cellular transplantation due to the lowered risk of oncogenesis.

<Experiment 3> Preparation of Spinal Cord-Injured Mice, Cellular Transplantation Thereto, and Analysis of the Transplanted Mice In this example, model mice of spinal cord injury were made by inducing traumatic spinal cord injury of the spinal nerve at the 10th thoracic vertebral level, and used for transplantation of tertiary neurospheres derived from human iPS cells to demonstrate an enhanced recovery, as described below.

First, 8- to 9-week-old NOD/SCID female mice (weighing 20 to 22 g) were anesthetized with ketamine (100 mg/kg) and xylazine (10 mg/kg). After laminectomy of the 10th thoracic vertebra, the dorsal surface of the dura mater was exposed, and traumatic spinal cord injury was produced using Infinite Horizon Impactor (60 kdyn; Precision Systems, Kentucky, Ill.).

To transplant cells to the injured spinal cord, the injury site was exposed again at 9 days after the injury. The cells of $5 \times 10^5$ cells/2 ul were introduced into the center of the lesioned area at a rate of 0.5 ul/min using a glass micropipette mounted on a stereotaxic injector (KDS310, Muromachi-kikai, Tokyo, Japan). In this example, clones of 253G1 and 201B7 for the iPS-TNSs and a clone of KhES1 for the ES-SNS were used, and their respective neurospheres were partially dissociated prior to their transplantations. As a control, PBS (vehicle) was injected in the same method as the cellular transplantation.

The motor function of hindlimbs was evaluated by the Basso-Beattie-Bresnahan (BBB) score (NPL 12) at every seven days till Day 42. The results are shown in FIG. 3.

In all the four groups, mice were completely paralyzed immediately after the induction of the spinal cord injury, but they all gradually recovered. However, after 3 weeks from the operation, the same degree of recoveries were observed in both the iPS-TNS and the ES-SNS-transplanted groups by comparing the BBB scores, with a significant difference from the group which received only the medium without cells. Also in clinical observations, the iPS-TNS-transplanted mice exhibited marked recovery sufficient for weight-supporting plantar stepping.

In conclusion, a nerve injury of a spinal cord-injured mouse can be treated by trans-planting neurospheres derived from human iPS cells even in the state not to differentiate into glial cells in vitro.

<Experiment 4> Comparison of the Differentiation and Proliferation Properties Between the Neurospheres Differentiated from the EBs with and without LIF Primary, secondary and tertiary neurospheres were formed, allowed to differentiate into neural cells and their cell-types were analyzed according to methods described in Experiment 1.

As a result shown in FIG. 4, in all of the three clones, neurons indicated by green fluorescence were differentiated with and without LIF, while astrocytes indicated by red fluorescence were differentiated without LIF but not with LIF. Thus, by culturing the EBs and neurospheres in the medium with LIF, the subcultured neurospheres maintain the differentiation property that they can differentiate substantially only into neurons but not into glial cells.

It should be noted that the neurospheres grew more rapidly in the medium with LIF than in the medium without LIF. An example using 201B7 is shown in FIG. 5. It is clear that neurospheres cultured with LIF are generally bigger than those cultured without LIF.

<Experiment 5> Subtypes of Neurons that Differentiate from the Higher-Order Neurospheres Cultured in LIF-Containing Medium Tertiary neurospheres of an human iPS clone 201B7 and an human ES clone KhES1 (control) were formed, allowed to differentiate into neural cells and subtypes were analyzed for the differentiated neurons using marker antibodies according to methods described in Experiment 1. The antibodies used in this experiment are: anti-Islet-1 (39.4D5, mouse IgG2b, 1:200, Developmental Studies of Hybridoma Bank: DSHB), anti-beta III-tubulin (SIGMA T8660 mouse IgG2b, 1:1000), anti-CNPase (SIGMA C5922, mouse IgG1, 1:1000), anti-GFAP (rabbit IgG, DAKO Z0334, rabbit IgG, 1:4000), anti-TH-1 (Chemicon AB152, rabbit IgG, 1:100). CNPase and GFAP are glial markers for oligodendrocytes and astrocytes, respectively. Islet-1 and TH-1 are markers for early-born neurons.

As shown in FIG. 6, almost all of the differentiated cells are beta III-tubulin-positive neuronal cells, and CNPase- or GFAP-positive glial cells did not differentiate from the tertiary neurospheres. As for the subtypes of the neuronal cells, Islet-1- or TH-1-positive neurons differentiated, indicating that the differentiated neurons are early-born-type neurons.

INDUSTRIAL APPLICABILITY

Culture conditions of embryoid bodies and/or neural stem cells derived from human differentiated cell-derived pluripotent stem cells, which are appropriate for neuronal differentiation of the neural stem cells were developed by the present invention.

The invention claimed is:

1. A method for culturing a human neural stem cell, comprising the step of providing a human neural stem cell that has been determined to express CD56 and to not express TRA-1-60 and TRA-1-81, and culturing the human stem cell in a medium containing LIF (Leukemia Inhibitory Factor).

2. The method of claim 1, wherein the LIF concentration is from 10 to 100 ng/ml.

3. The method of claim 1, wherein the human neural stem cell is obtained by differentiation of a human differentiated cell-derived pluripotent stem cell or a human embryonic stem cell.

4. The method of claim 1, further comprising differentiating the cultured neural stem cell into a neuronal cell.

5. A method for obtaining a secondary or higher-order neurosphere comprising a human neural stem cell, comprising
culturing an embryoid body derived from a human pluripotent stem cell in a medium containing LIF to obtain a primary neurosphere comprising a human neural stem cell and determining that the human stem cell expresses CD56 and does not express TRA-1-60 and TRA-1-81;
culturing the primary neurosphere according to claim 1;
subculturing the primary neurosphere in a medium containing LIF at least one time; and
obtaining a secondary or higher-order neurosphere comprising a human neural stem cell.

6. The method of claim 5, wherein the LIF concentration is from 10 to 100 ng/ml.

7. The method of claim 5, wherein the human neural stem cell is obtained by differentiation of a human differentiated cell-derived pluripotent stem cell or a human embryonic stem cell.

8. The method of claim 5, further comprising differentiating the cultured neural stem cell into a neuronal cell.

* * * * *